United States Patent
Mosier et al.

(10) Patent No.: US 11,008,298 B2
(45) Date of Patent: May 18, 2021

(54) SYNTHESIS OF 5-HYDROXYMETHYLFURFURAL

(71) Applicant: Purdue Research Foundation, West Lafayette, IN (US)

(72) Inventors: Nathan Scott Mosier, West Lafayette, IN (US); Jonathan Christopher Overton, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/866,681

(22) Filed: May 5, 2020

(65) Prior Publication Data

US 2020/0369635 A1 Nov. 26, 2020

Related U.S. Application Data

(60) Provisional application No. 62/852,599, filed on May 24, 2019.

(51) Int. Cl.
*C07D 307/50* (2006.01)

(52) U.S. Cl.
CPC .................................. *C07D 307/50* (2013.01)

(58) Field of Classification Search
None
See application file for complete search history.

(56) References Cited

FOREIGN PATENT DOCUMENTS

CN 102911142 B 4/2015

OTHER PUBLICATIONS

Zhang, Ximing, "Effect of maleic acid on the selectivity of glucose and fructose dehydration and degradation", Open Access Dissertations. 609. (Year: 2015).*
Zhou et al., Conversion of glucose into 5-hydroxymethylfurfural in different solvents and catalysts: Reaction kinetics and mechanism. Egyptian Journal of Petroleum, vol. 26, Issue 2, Jun. 2017, pp. 477-487.

* cited by examiner

*Primary Examiner* — Zinna Northington Davis
(74) *Attorney, Agent, or Firm* — Purdue Research Foundation; Zhigang Rao

(57) ABSTRACT

The present disclosure relates to a novel and improved synthesis of 5-hydroxymethylfurfural (HMF) from a glucose source. The synthesis of 5-hydroxymethylfurfural (HMF) is carried out by reacting a mixture comprising a Brønsted acid, a Lewis acid, water, dimethyl sulfoxide (DMSO), acetonitrile, and a glucose source.

7 Claims, 1 Drawing Sheet

SYNTHESIS OF 5-HYDROXYMETHYLFURFURAL

GOVERNMENT RIGHTS

This invention was made with government support under Award No. DE-SC0000997 awarded by the Department of Energy (DOE). The United States government has certain rights in the invention.

TECHNICAL FIELD

The present disclosure relates to a novel and improved synthesis of 5-hydroxymethylfurfural (HMF) from a glucose source.

BACKGROUND

This section introduces aspects that may help facilitate a better understanding of the disclosure. Accordingly, these statements are to be read in this light and are not to be understood as admissions about what is or is not prior art.

Photo-synthetically-derived carbohydrates are a promising platform for producing fuels and chemicals with improved functionality over petroleum-based products and will facilitate a reduction in the petroleum required for commodity chemical production. In a well-established industrial process, these carbohydrates can be obtained from starch through the process of hydrolysis to glucose. Corn-derived glucose is a promising candidate to produce low-carbon fuels and chemicals and warrants further research and development as a production platform for commodity chemicals and fuels.

One of these valuable platform chemicals is 5-hydroxymethylfurfural (HMF), which can be used to produce plastics, adhesives, fuels, and pharmaceuticals. One of the notable products that can be produced from HMF is 2,5-furandicarboxylic acid (FDCA), which can replace terephthalic acid in the production of poly(ethylene terephthalate) (PET), which becomes poly(ethylene 2,5-furandicarboxylate) (PEF) when FDCA is used in place of terephthalic acid. In addition to being renewably sourced, PEF is also more lightweight and has better gas barrier properties than PET, making it a promising sustainable plastic for food and beverage packaging applications.

The majority of previously described processes for the production of HMF from renewable sources focus on dehydration of bio-derived fructose. Since fructose is typically produced from glucose, using glucose to directly produce HMF would lead to more economical processes by bypassing production of fructose in a separate reaction.

Because the commercializing production of 5-hydroxymethylfurfural (HMF) from glucose has been hindered by low consumption of glucose and moderate HMF yields and selectivity, an improved method of converting glucose to HMF would be desirable.

SUMMARY

The present invention provides a novel and improved synthesis of 5-hydroxymethylfurfural (HMF).

In one embodiment, the present disclosure provides a method of synthesizing 5-hydroxymethylfurfural (HMF), wherein the method comprises reacting a mixture comprising a Brønsted acid, a Lewis acid, water, dimethyl sulfoxide (DMSO), acetonitrile, and a glucose source.

DETAILED DESCRIPTION

Figure 1:
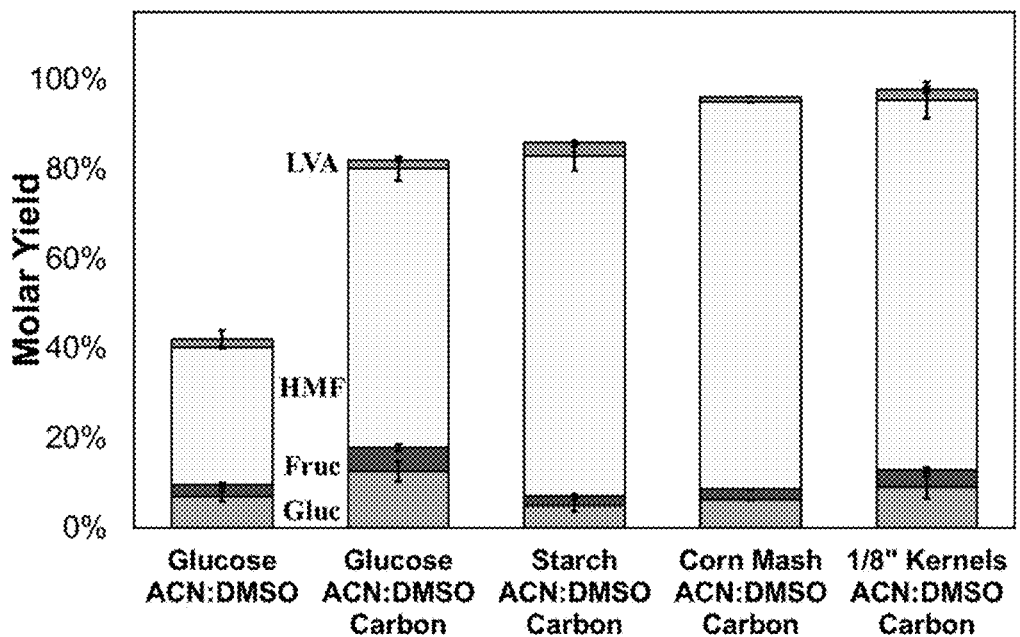
FIG. 1: HMF yields in co-solvent mixtures with and without activated carbon. All substrates were loaded at 30 wt %.

For the purposes of promoting an understanding of the principles of the present disclosure, reference will now be made to embodiments illustrated in drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

In the present disclosure the term "glucose source" refers to any material that may comprise glucose, or a polymeric form of glucose. A glucose source may include but is not limited to glucose, cane sugar, cracked corn, milled corn, corn starch, corn mash, or any combination thereof. The polymeric form of glucose may be degraded to glucose under acid or basic hydrolysis conditions.

In the present disclosure the term "adsorbent" refers to a natural organic or a natural inorganic material, or a synthetic material that is capable of allowing material to be adsorbed onto the adsorbent. Non-limiting examples may include but is not limited to activated carbon, natural clay, bauxite, silica gel, activated charcoal, peat, hay, vegetable fibers, feathers, kapok, sawdust, milkweed, straw, or any combination thereof.

In the present disclosure the term "Brønsted acid" refers to an acid that is a proton (H+ ion) donor. Non-limiting example of Brønsted acids may be but is not limited to an inorganic acid such as HCl, on organic acid such as maleic acid, or any combination thereof.

In the present disclosure the term "Lewis acid" refers to an electron pair acceptor. An example of a Lewis acid may be but is not limited to $AlCl_3$, $BF_3$, or any combination thereof.

In one embodiment, the present disclosure provides a method of synthesizing 5-hydroxymethylfurfural (HMF), wherein the method comprises reacting a mixture comprising a Brønsted acid, a Lewis acid, water, dimethyl sulfoxide (DMSO), acetonitrile, and a glucose source.

In one embodiment regarding the method of synthesizing 5-hydroxymethylfurfural (HMF), wherein the glucose source comprises glucose, cane sugar, cracked corn, milled corn, corn starch, corn mash, or any combination thereof.

In one embodiment regarding the method of synthesizing 5-hydroxymethylfurfural (HMF), wherein the method is carried out by providing a first mixture comprising the Brønsted acid, the Lewis acid, water, dimethyl sulfoxide (DMSO), acetonitrile; and then by adding the glucose source to the first mixture followed by reacting at the elevated temperature.

In one embodiment regarding the method of synthesizing 5-hydroxymethylfurfural (HMF), wherein the Brønsted acid comprises maleic acid.

In one embodiment regarding the method of synthesizing 5-hydroxymethylfurfural (HMF), wherein the Lewis acid comprises $AlCl_3$.

In one embodiment regarding the method of synthesizing 5-hydroxymethylfurfural (HMF), wherein the mixture further comprises a solid adsorbent. In one aspect, the solid adsorbent comprises activated carbon.

In one embodiment regarding the method of synthesizing 5-hydroxymethylfurfural (HMF), wherein DMSO has a volume/volume percentage of about 30-50%, acetonitrile has a volume/volume percentage of about 10-30%, and the glucose source has a weight percentage of about 20-40%. In one aspect, DMSO has a volume/volume percentage of about 35-45%, acetonitrile has a volume/volume percentage of about 15-25%, and the glucose source has a weight percentage of about 25-35%.

In one embodiment regarding the method of synthesizing 5-hydroxymethylfurfural (HMF), wherein the synthesizing of 5-hydroxymethylfurfural (HMF) is carried out at a temperature range of about 150-250° C., and the synthesizing of 5-hydroxymethylfurfural (HMF) is substantially accomplished within about 2-30 minutes. In one aspect, the synthesizing of 5-hydroxymethylfurfural (HMF) is carried out at a temperature range of about 180-250° C., and the synthesizing of 5-hydroxymethylfurfural (HMF) is substantially accomplished within 2-10 minutes.

In one embodiment regarding the method of synthesizing 5-hydroxymethylfurfural (HMF), wherein the glucose source comprises glucose, cane sugar, cracked corn, milled corn, corn starch, corn mash, or any combination thereof.

Materials and Methods

Materials and General Reaction Conditions

Glucose, fructose, levulinic acid (LVA), HMF, maleic acid, $AlCl_3$, acetonitrile, and DMSO were all purchased form Sigma-Aldrich (St. Louis, Mo., USA). Stainless steel reactors for conducting reactions were used as described in previous works. See Zhang, X.; Hewetson, B. B.; Mosier, N. S. Kinetics of Maleic Acid and Aluminum Chloride Catalyzed Dehydration and Degradation of Glucose. *Energy and Fuels* 2015. The reaction media included co-solvent concentrations of 20% (v/v) DMSO and 40% (v/v) acetonitrile in water). Substrates (glucose source such as glucose, starch, corn mash, 1.375 mm dry-milled corn) are loaded to at 30 wt % and vigorously mixed before reacting. All substrates were dried at 45° C. prior to use. Briefly, reactions were performed in 316 L stainless steel tubing (8 mm diameter, 2.1 mm wall thickness, 70 mm length) and fitted with 1.2 cm Swagelok end fittings (Swagelok, Solon, Ohio, USA). Reactors had a volume of ~3.5 mL and were filled with 2 mL of reaction solution, allowing for gas and liquid expansion within the reactor.

Reaction Procedures

Reaction from Glucose/Starch, 2 mL Scale

A mixture of 50 mM maleic acid and 100 mM aluminum chloride in a solution of water, DMSO, and acetonitrile is prepared as the reaction solution. The volume of acetonitrile is 40% the total volume, and the volume of DMSO is 20% of the total volume. Add 1.6 grams of this mixture to a stainless steel reaction tube (reactor volume is ~2.3 ml). Then, add 0.6 g of glucose or starch to the reactor. Next, add 0.2 g of activated carbon and 0.2 g of NaCl. Seal the reactor tightly and vigorously shake the reactor to mix materials. Place the reactor in a sand bath at a temperature of 180° C. It takes about 2 minutes for the solution to reach 180° C. After the 2 minutes, the reactor is held at 180° C. for 3 minutes (total time in sand bath of 5 minutes). The reactor is then removed and placed in ice water for quick cooling. Next, the reactor is opened and the reaction media is filtered for HPLC analysis.

Reaction from Glucose/Starch, 30 mL Scale

Add 21 g of reaction solution to the reactor (reactor volume is ~40 ml). Next, add 9 g of starch or glucose to the reactor. Then add 3 g of activated carbon and 3 g of NaCl. Tightly seal the reactor and vigorously mix the reactor by shaking. Place the reactor in the sand bath at 230° C. for 135 seconds, then place it in a sand bath at 180C. After the reactor reaches temperature (150 seconds), wait 3 minutes and then cool the reactor in ice water. Remove the reactor seal and filter samples for HPLC analysis.

Similar reactions are carried out for dry-milled corn and corn mash. The yield of HMF from glucose is about 60%. The yield of HMF from starch is about 75%. The yield of HMF from corm is about 80-85%.

Reaction Pathway

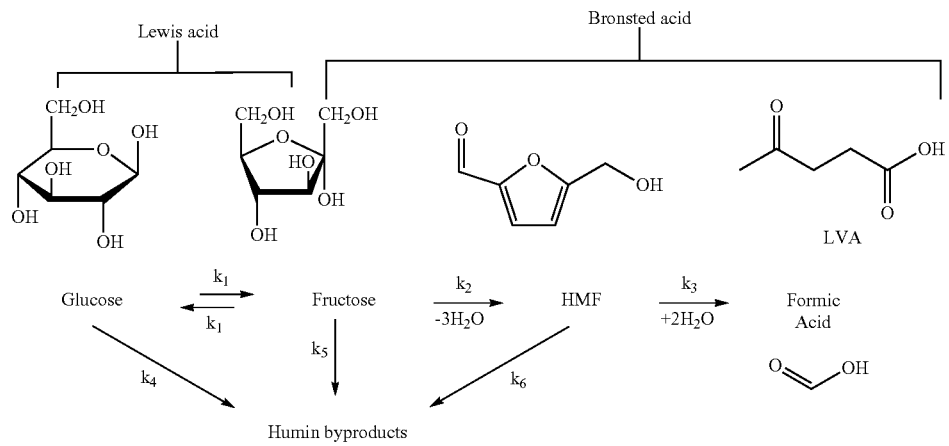

Scheme 1. Reaction pathway for the conversion of glucose to HMF. Glucose is first isomerized to fructose in a reaction catalyzed by a Lewis acid ($AlCl_3$). Then, fructose is dehydrated to HMF by maleic acid, which acts as a Brønsted acid. HMF can be additionally rehydrated to LVA. Each reactant can undergo parallel side reactions to undesired side products, known as humins. See Zhang, X.; Hewetson, B. B.; Mosier, N. S. Kinetics of Maleic Acid and Aluminum Chloride Catalyzed Dehydration and Degradation of Glucose. *Energy and Fuels* 2015. (Zhang et al.)

Kinetic Modeling

It was first assumed that all reactors were well mixed and completely isothermal during reactions after heat-up. A system of differential equations were derived using a monophasic model assuming first order reaction kinetics, as shown in Scheme 1 and equations 1-4 as described by Zhang et al. In this reaction, glucose is isomerized by $Al^{3+}$ to fructose.

$$\frac{d[Glucose]}{dt} = -(k_1 + k_4)[Glucose] + k_{-1}[Fructose] \quad (1)$$

$$\frac{d[Fructose]}{dt} = -(k_2 + k_5)[Fructose] + k_1[Glucose] \quad (2)$$

$$\frac{d[HMF]}{dt} = -(k_3 + k_6)[HMF] + k_2[Fructose] \quad (3)$$

$$\frac{d[LVA]}{dt} = k_3[HMF] \quad (4)$$

For kinetic analysis, reactions were performed at temperatures of 120, 140, and 160° C. using glucose (250 mM), fructose (250 mM), and HMF (60 mM) separately as substrates to allow determination of individual reaction rates. Reaction solution (2 mL) was placed in the stainless steel reactor and the reactor was sealed tightly. Reactors were then immersed in a sand bath for the desired reaction time, with an additional two minutes of heat-up. Immediately after the reaction time ended, reactors were removed from the sand bath and immersed in cool water. Reaction solution was then filtered through a 0.2 μm nylon filter and diluted for high pressure liquid chromatography (HPLC). HPLC was performed on an HPX-87H AMINEX column (BioRad, Hercules, Calif., USA) with a mobile phase of 10 mM $H_2SO_4$ in water and 5% (w/w) acetonitrile. Acetonitrile and an increased $H_2SO_4$ concentration were used to facilitate the separation of glucose from maleic acid and fructose from malic acid. The flow rate through the Waters 1525 pump and Waters 2412 Refractive Index Detector (Waters Corp. Milford, Mass., USA) was 0.6 mL per minute with a column temperature of 65° C. The concentration of all reactants and products was determined by external calibration standards. For reactions with 30 wt. % glucose, 0.6 g of glucose was first placed in the reactor tube. Reaction solution with the desired catalyst and co-solvent concentration was then added to bring the total mass added to the reactor to 2 g. Dilutions for these reactions were performed on a weight basis, since it could no longer be assumed that the density of the reaction solution was that of water to allow for volumetric dilutions. Samples were diluted 40-50×, to ensure that all components were less than 2 g/L for HPLC analysis. After this dilution was performed, it was assumed that the density of this solution was equal to the density of water for calculating the mass of solute present.

Co-Solvent Screening

It has been well-established that the use of polar, aprotic solvents in combination with water increase the yield of HMF. However, the effect of these solvents on maleic acid:$AlCl_3$ catalyst systems has not been determined. First, a screen of common polar, aprotic solvents at concentrations of 10 and 20% (v/v) was performed to determine the effect of each solvent on HMF yield from 30% (wt.) glucose. The first criteria for co-solvent selection was HMF yield. Among many screened solvents, DMSO resulted in the highest HMF yield from glucose. Additionally, previous work has shown the reactions of glucose and fructose to humins to be second order. In hopes of reducing the loss of sugars to humins throughout the reaction, acetonitrile was found among many screened solvents as the second solvent because it was found that acetonitrile may have altered the rate of isomerization of glucose to fructose. Therefore, the combination of DMSO and acetonitrile may increase sugar conversion, reduce humin formation from sugars, and increase overall HMF yield from glucose.

To better understand the role of DMSO in increasing HMF yield in maleic acid and $AlCl_3$-catalyzed HMF production, a full kinetic analysis of each reaction step was performed with no DMSO, 10% DMSO, and 20% DMSO. It was found that the increasing of DMSO concentration led to an increase in the rate of fructose dehydration while simultaneously reducing the rate of humin and LVA formation from HMF. While the altered reaction kinetics did not significantly alter the rate of glucose isomerization to fructose, the increased rate of fructose consumption resulted in a shift of the equilibrium concentrations of glucose and fructose towards fructose. The net effect of this was a decrease in unreacted glucose from 30% to 20% at 12 minutes for reactions with no DMSO and 20% DMSO, respectively. This increased disappearance of glucose also correlates to an increase in HMF yield from 29% to 40% when 20% (v/v) DMSO is added. The selectivity of HMF formation to HMF degradation increased from 3.3 to 13.9 with addition of 20% DMSO at 160° C. To validate the accuracy of our kinetic model, the concentration of glucose, fructose, HMF, and LVA at times outside of the initial reaction times was used to determine kinetic rates. For reactions conducted both with and without DMSO, the model predicts the profile of each reaction component with reasonable accuracy. To further validate the model, the model was evaluated against reactions performed with 30 wt. % glucose as substrate. The fit of the model at elevated substrate concentrations further confirms that each reaction is first order results in a model that can accurately predict yields, even though it has been determined experimentally that the formation of humins is second order.

The ratio of Brønsted acid to Lewis acid may significantly alter reaction rate, selectivity, and yield during HMF production. In light of this concern, a results-driven optimization of the catalyst system was conducted for HMF yield and glucose consumption. The concentration of $AlCl_3$ was first held constant at 100 mM and varied maleic acid concentration from 20 to 500 mM to represent ratios of 1:5, 1:2, 1:1, 2:1, and 5:1 maleic acid:$AlCl_3$. Each of these ratios was evaluated for glucose consumption, HMF yield, and LVA yield at 160° C. for 12 minutes. By evaluating the consumption of glucose as well as the ratio of HMF yield to LVA yield, the relative rate of each catalyst ratio relative to other ratios can be determined. As maleic acid concentration was increased, the consumption of glucose was decreased significantly. This aligns with previous results which demonstrate that maleic acid likely shields glucose from further degradation.

Next, the concentration of maleic acid was held constant at 100 mM while $AlCl_3$ was varied from 20 mM to 250 mM. An increase in Lewis acid concentration resulted in increased rate of glucose isomerization to fructose. However, the yield of HMF did not increase at the same rate as glucose isomerization, likely due to increased humin formation catalyzed by a high Lewis acid concentration. Similar screens was conducted to hold maleic acid concentration constant at 20 and 50 mM to optimize the lowest catalyst loading for greatest HMF yield. From this study, it was determined that greatest conversion of glucose and highest yield of HMF was reached with an AlCl$_3$ concentration of about 100 mM and a maleic acid concentration of about 50 mM.

Fructose is subsequently dehydrated to HMF, which can be partially rehydrated to LVA. Each reaction step can also result in the formation of insoluble humins and degradation products. Each rate was estimated using linear regression in Microsoft Excel. For each substrate, data points were only used if the substrate concentration was greater than 75% of the initial substrate concentration, to obtain only initial reaction rates and rule out effects of secondary reactions. A minimum of three time points, with duplicate reactions, were used for each rate regression. At reaction temperatures not evaluated during development of the model, kinetic rates were predicted by the Arrhenius equation using experimentally determined activation energies and kinetic rates measured at 120° C. as a reference temperature. MATLAB was used to simulate reactions according to a $4^{th}$ order Runge-Kutta integration of reaction equations.

After catalyst optimization, the use of DMSO to increase HMF yield at predicted reaction optima (195° C., 2 minutes) was still less than 30%. This low yield was in part caused by a slow rate of glucose isomerization relative to other reactions. During the solvent screen, it was hypothesized that acetonitrile may increase the rate of glucose isomerization to fructose. To test this hypothesis, a full kinetic evaluation of HMF production was performed from glucose in the presence of 20 and 40% (v/v) acetonitrile in water. Interestingly, the rate of glucose isomerization is not increased substantially between 0 and 20% acetonitrile. However, it was unexpectedly found that at 40% acetonitrile, the rate of glucose isomerization is increased by almost 60%. Additionally, the rate of fructose isomerization to glucose was reduced by almost 50%. This unexpected result suggests that acetonitrile shifts the equilibrium of glucose and fructose towards fructose. The increase in glucose isomerization was also accompanied by an increase in the rate of humin formation from glucose by more than 4×.

During kinetic analysis of the isomerization of glucose to fructose in acetonitrile, it was observed that acetonitrile concentrations of 20% (v/v) did not significantly alter isomerization rates, while at 40% acetonitrile these rates were almost doubled. To better understand the cause of this observation, the molecular dynamic simulations were used to investigate differences in glucose solvation as a function of acetonitrile concentration. The solvation of water and acetonitrile was represented by the simulated average occupancy of the oxygen in water and the nitrogen in acetonitrile around each atom of beta-glucose in the ring form. Using this simulation data, the radial distribution function (RDF) was evaluated for water oxygen and acetonitrile nitrogen around each carbon and oxygen atoms in glucose. By comparing the RDF of water and acetonitrile around each carbon, the relative impact of acetonitrile content on glucose solvation could be determined.

About 20% (v/v) DMSO, 40% (v/v) acetonitrile, 50 mM maleic acid, and 100 mM AlCl$_3$ were combined to produce HMF from 30 wt. % glucose. It was unexpectedly found that the concentrations of glucose, fructose, and LVA were reduced in the presence of both DMSO and acetonitrile. A molar HMF yield of 30% was reached at a ratio of 16.7 moles of HMF to moles of LVA. In addition to the co-solvent system, the addition of activated carbon to the reaction solution of glucose resulted in conversion of 30 weight percent glucose to HMF at molar yields of 62%. When the system is applied with glucose sources comprising starch, enzymatically-liquefied corn, and milled corn, the molar HMF yields is obtained as high as 85%.

Figure 2:
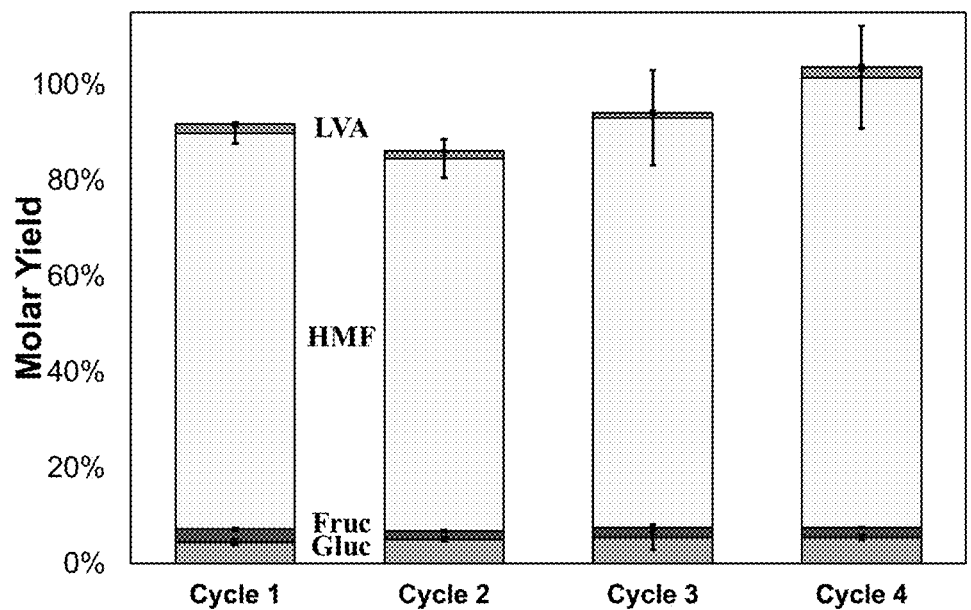
FIG. 2: Conversion of dry-milled corn to HMF after recycling activated carbon through a diethyl ether washing step.

To reduce unit operations required for an industrial production facility, The present disclosure provides a one-pot reaction of converting a 30 wt % glucose to HMF in a reactor with 10% activated carbon added to the reaction (FIG. 1). Including activated carbon in the liquid media increased the molar yield of HMF from glucose by almost two times. In light of this improvement in conversion yields, the conversion of purified starch, enzymatically-liquefied corn mash, and dry-milled corn kernels to HMF in a one-pot reaction was also investigated. Notably, dry-milled corn kernels milled to ⅛ inch (3.175 mm) were converted to HMF at molar efficiencies of 88%. After reactions, 20-50 mg of HMF was extracted from each gram of activated carbon using either diethyl ether (DEE) or ethanol. Since HMF is a valuable product, the HMF remaining in the carbon was extracted after reactions using a DEE wash with the same volume of DEE as reaction media. It was demonstrated that up to 4 cycles of reactions and washings could be repeated with no significant loss of reaction yield in each cycle (FIG. 2).

This disclosure systematically evaluated solvents for increased yield and selectivity in maleic acid and AlCl$_3$-catalyzed conversion of glucose to HMF. A novel and improved method of synthesizing HMF from a glucose source in a unique DMSO/acetonitrile/water solvent system has been identified. The impact of acetonitrile and DMSO was each individually evaluated on the kinetics of each reaction step. It was found that DMSO can more than double the rate of fructose dehydration while also strongly inhibits rehydration of HMF to LVA. Additionally, 40% acetonitrile almost doubles the rate of glucose isomerization to fructose. It has been demonstrated that HMF can be produced from 30 wt. % glucose at molar yields as high as 30%. Through additional analyses, it has been demonstrated that the limiting factor for HMF yield is the solubility of HMF in the reaction liquid. Through this work, a framework has been provided to reduce second order reactions of glucose and fructose to humins by reducing their concentration in the reaction mixture. This is achieved through the addition of acetonitrile to increase the rate of glucose isomerization and DMSO to increase the rate of fructose dehydration.

Those skilled in the art will recognize that numerous modifications can be made to the specific implementations described above. The implementations should not be limited to the particular limitations described. Other implementations may be possible.

We claim:

1. A method of synthesizing 5-hydroxymethylfurfural (HMF) from a glucose source, wherein the method comprises reacting a mixture comprising a Brønsted acid, a Lewis acid, water, dimethyl sulfoxide (DMSO), acetonitrile, activated carbon, and a glucose source.

2. The method of claim 1, wherein the method is carried out by providing a first mixture comprising the Brønsted acid, the Lewis acid, water, dimethyl sulfoxide (DMSO), acetonitrile; and then by adding the glucose source and said activated carbon to the first mixture.

3. The method of claim 1, wherein the Brønsted acid comprises maleic acid.

4. The method of claim 1, wherein the Lewis acid comprises AlCl$_3$.

5. The method of claim 1, wherein DMSO has a volume/volume percentage of 10-30%, acetonitrile has a volume/volume percentage of 30-50%, and the glucose source has a weight percentage of 20-40%.

6. The method of claim 1, wherein the synthesizing of 5-hydroxymethylfurfural (HMF) is carried out at a temperature range of 150-250° C., and the synthesizing of 5-hydroxymethylfurfural (HMF) is substantially accomplished within 2-30 minutes.

7. The method of claim 1, wherein the glucose source comprises glucose, cane sugar, cracked corn, milled corn, corn starch, corn mash, or any combination thereof.

* * * * *